(12) United States Patent
Wilzbach et al.

(10) Patent No.: US 10,324,281 B2
(45) Date of Patent: Jun. 18, 2019

(54) SURGICAL MICROSCOPE HAVING A DATA UNIT AND METHOD FOR OVERLAYING IMAGES

(71) Applicant: Carl Zeiss Meditec AG, Jena (DE)

(72) Inventors: Marco Wilzbach, Stuttgart (DE); Stefan Saur, Aalen (DE); Gerald Panitz, Ellwangen (DE)

(73) Assignee: Carl Zeiss Meditec AG, Jena (DE)

( * ) Notice: Subject to any disclaimer, the term of this patent is extended or adjusted under 35 U.S.C. 154(b) by 50 days.

(21) Appl. No.: 15/361,286

(22) Filed: Nov. 25, 2016

(65) Prior Publication Data

US 2017/0082847 A1 Mar. 23, 2017

Related U.S. Application Data

(63) Continuation of application No. PCT/EP2015/061262, filed on May 21, 2015.

(30) Foreign Application Priority Data

May 27, 2014 (DE) .................... 10 2014 210 053

(51) Int. Cl.
*G02B 21/36* (2006.01)
*G02B 21/00* (2006.01)
(Continued)

(52) U.S. Cl.
CPC ............ *G02B 21/367* (2013.01); *A61B 34/20* (2016.02); *A61B 90/20* (2016.02);
(Continued)

(58) Field of Classification Search
CPC .................................................. G02B 21/367
See application file for complete search history.

(56) References Cited

U.S. PATENT DOCUMENTS 5,345,538 A 9/1994 Narayannan et al.
7,688,503 B2 3/2010 Hermann et al.
(Continued)

FOREIGN PATENT DOCUMENTS

DE 10 2009 018 633 A1 10/2010

OTHER PUBLICATIONS

Translation of the Office action of the German Patent Office dated Feb. 11, 2015 of German patent application 10 2014 210 053.4 on which this application is based.
(Continued)

*Primary Examiner* — Rowina J Cattungal
(74) *Attorney, Agent, or Firm* — Walter Ottesen, P.A.

(57) ABSTRACT

A surgical system has a surgical microscope with an imaging optical unit and a control unit for setting imaging parameters of the microscope. The system further has an image processing device for overlaying an overlay image stored in the image processing device with an image generated by the microscope. A data processing unit is connected to the control unit of the microscope and to the image processing device. The control unit is configured such that, before a change of at least one imaging parameter of the microscope from a first value to a second value, it stores both the first value and the second value and makes them available to the data processing unit. The image processing device is configured in such a manner that it modifies the overlay image in a manner corresponding to the stored first and second values of the at least one imaging parameter.

6 Claims, 5 Drawing Sheets

(51) Int. Cl.
  *G02B 21/22*   (2006.01)
  *A61B 34/20*   (2016.01)
  *H04N 5/232*   (2006.01)
  *H04N 5/265*   (2006.01)
  *A61B 90/20*   (2016.01)

(52) U.S. Cl.
  CPC ......... *G02B 21/0012* (2013.01); *G02B 21/22* (2013.01); *H04N 5/23216* (2013.01); *H04N 5/265* (2013.01)

(56) References Cited

U.S. PATENT DOCUMENTS

| | | | |
|---|---|---|---|
| 8,976,238 B2 | 3/2015 | Emsperger et al. | |
| 2003/0227673 A1* | 12/2003 | Nakagawa | G02B 21/241 |
| | | | 359/380 |
| 2004/0070822 A1* | 4/2004 | Shioda | A61B 1/04 |
| | | | 359/372 |
| 2006/0293557 A1* | 12/2006 | Chuanggui | A61B 90/36 |
| | | | 600/101 |
| 2012/0323228 A1* | 12/2012 | Peyman | A61F 9/00821 |
| | | | 606/4 |
| 2013/0006270 A1* | 1/2013 | Schmoll | A61B 34/25 |
| | | | 606/130 |
| 2015/0181131 A1 | 6/2015 | Kerwien et al. | |

OTHER PUBLICATIONS

International Search Report dated Aug. 3, 2015 of international application PCT/EP2015/061262 on which this application is based.

\* cited by examiner

| Step | | |
|---|---|---|
| Standard settings |  | |
| Settings for producing Blue 400 modality. Specifically, here the illumination settings are changed. |  | |
| Resultant tumor margin modality. This is valid for the settings during the recording. |  | |
| Augmentation of situs and modality |  | |
| Change of zoom |  |  |
| Adaptation of modality |  |  |
| Augmentation of situs and modality |  | |

SURGICAL MICROSCOPE HAVING A DATA UNIT AND METHOD FOR OVERLAYING IMAGES

CROSS REFERENCE TO RELATED APPLICATIONS

This application is a continuation application of international patent application PCT/EP2015/061262, filed May 21, 2015, designating the United States and claiming priority from German application 10 2014 210 053.4, filed May 27, 2014, and the entire content of both applications is incorporated herein by reference.

FIELD OF THE INVENTION

The invention relates to a surgical system having a surgical microscope and an image processing device, which overlays the image generated by the surgical microscope with a further image.

BACKGROUND OF THE INVENTION

Intraoperative modalities (that is, diagnostic data obtained intraoperatively with sensors, such as for example functional brain mapping IOI, 5-ALA Fluorescence Blue 400, fluorescence tumor margin calculations, ICG fluorescence IR800, Flow 800, topography, 2D/3D image information, . . . ) are created at a certain point in time. Some modalities can be produced continuously (topography measurement), or repeatedly (Blue 400, tumor margin, IR800, Flow 800 . . . ), others only at certain points in time during the operation (IOI after opening of the dura, . . . ).

The recording of the modalities usually requires other settings (for example illumination, filter changes . . . ) or a change in the operating sequence. Normally, this setting is disjoint with the preferred settings during the resection from or during an intervention in the tissue.

A solution for displaying the information of the various modalities in the standard settings is offered by augmenting the optical image of the situs with the image information of one or more of the aforementioned modalities. The augmentation may take the form of an overlay of an electronically generated image from the data of the modality over the optical image, for example with the aid of a splitter mirror. In the case of a purely electronic display (for example a monitor), the mixing may be accomplished purely digitally (without a splitter mirror) (video signal of the situs and the modality).

One disadvantage of this is that the modalities are only valid at a certain point in time or only with the settings with which the image was taken (zoom, focus, position (relative position of the surgical microscope with respect to the patient), . . . ). If these settings are changed, the data of the modality lose their validity, the overlay is no longer meaningful and must be ended. Some augmentations are only valid for a very short time.

It would therefore be expedient to extend the time interval of the valid augmentation.

SUMMARY OF THE INVENTION

It is an object of the invention to make the augmentation of intraoperative modalities valid for a longer time and more robust.

The object can, for example, be achieved by a surgical system including: a surgical microscope including an imaging optic and a control unit configured for setting imaging parameters of the surgical microscope; the surgical microscope being configured to generate an image; an image processing device configured to superimpose an overlay image stored in the image processing device to the image generated by the surgical microscope; a data processing unit connected to the control unit of the surgical microscope and the image processing device; the control unit being further configured to, before a change of at least one of the imaging parameters from a first value to a second value, store both the first value and the second value and provide the first value and the second value to the data processing unit; and, the data processing unit being configured to modify the overlay image in a manner corresponding to the first value and the second value of the at least one imaging parameter.

The object can, for example, further be achieved by a method for superimposing an overlay image with an image generated by a surgical microscope, the method including the steps of: superimposing the overlay image with the image generated by the surgical microscope; storing a first value and a second value of at least one imaging parameter of the surgical microscope; modifying the overlay image in a manner corresponding to the stored first and second values of the imaging parameter so as to generate a modified overlay image; changing the imaging parameter of the surgical microscope from the first value to the second value; and, overlaying the modified overlay image with the image generated by the surgical microscope.

A surgical system according to an embodiment includes a surgical microscope with an imaging optical unit and a control unit for setting imaging parameters of the surgical microscope. A stereoscopic or monoscopic surgical microscope may be used for this. Furthermore, an image processing device for overlaying an overlay image stored in the image processing device with an image generated by the surgical microscope is provided and may be arranged within a main body of the surgical microscope. A data processing unit is connected to the control unit of the surgical microscope and to the image processing device, it being possible for the data processing unit to be integrated with the surgical microscope or provided externally. The control unit is configured such that, before a change of at least one imaging parameter of the surgical microscope from a first value to a second value, it stores both the first value and the second value and makes them available to the data processing unit. As a result, with every refocusing, positional change and the like, both the "old" value and the "new" value of the imaging parameter to be changed are acquired and stored. The image processing device is configured in such a way that it modifies the overlay image in a way corresponding to the stored first and second values of the at least one imaging parameter. Via a suitable transformation function, which takes the changed values of the imaging parameter into account, the image processing device can therefore modify the overlay image in such a way that it can be overlaid on an image with the changed imaging parameter. This allows an augmentation to be achieved even with changed imaging parameters, so that intraoperative modalities can be displayed as an overlay image even when the imaging parameters of the surgical microscope have changed since the recording of the modalities.

According to some embodiments, the image processing device may also be configured such that, after a change of the imaging parameter from the first value to the second value, it overlays the modified overlay image with the image generated by the surgical microscope.

The control unit may be configured to store at least one time stamp together with the first and/or second value and make it available to the data processing unit.

A positioning system may be provided to position the surgical microscope at a predetermined spatial position, the positioning system being configured such that, before a change of a position value of the surgical microscope from a first position value to a second position value, it stores both the first position value and the second position value together with at least one time stamp and makes them available to the data processing unit.

The control unit may be configured in such a way that it only changes the at least one imaging parameter when the modified overlay image has been generated, so that the modified overlay image may be provided already before the change of the imaging parameter.

The at least one imaging parameter may be a setting parameter of the zoom, focus, position and alignment spatially of the surgical microscope and/or of the patient.

The data processing unit may be configured to provide at least one limit value for the value of the imaging parameter, the image processing device not generating a modified overlay image if the second value of the imaging parameter is beyond the limit value.

The overlay image may be overlaid with the image generated by the surgical microscope via at least one beam splitter.

The overlay image and the image generated by the surgical microscope may be respectively overlaid with one another as a video signal.

A method for overlaying an overlay image with an image generated by a surgical microscope according to an embodiment includes:

overlaying the overlay image with the image generated by the surgical microscope;
   storing a first value and a second value of at least one imaging parameter of the surgical microscope;
   modifying the overlay image in a way corresponding to the stored first and second values of the imaging parameter;
   changing the imaging parameter of the surgical microscope from the first value to the second value; and
   overlaying the modified overlay image with the image generated by the surgical microscope.

BRIEF DESCRIPTION OF THE DRAWINGS

The invention will now be described with reference to the drawings wherein.

DESCRIPTION OF THE PREFERRED
EMBODIMENTS OF THE INVENTION

Figure 1:
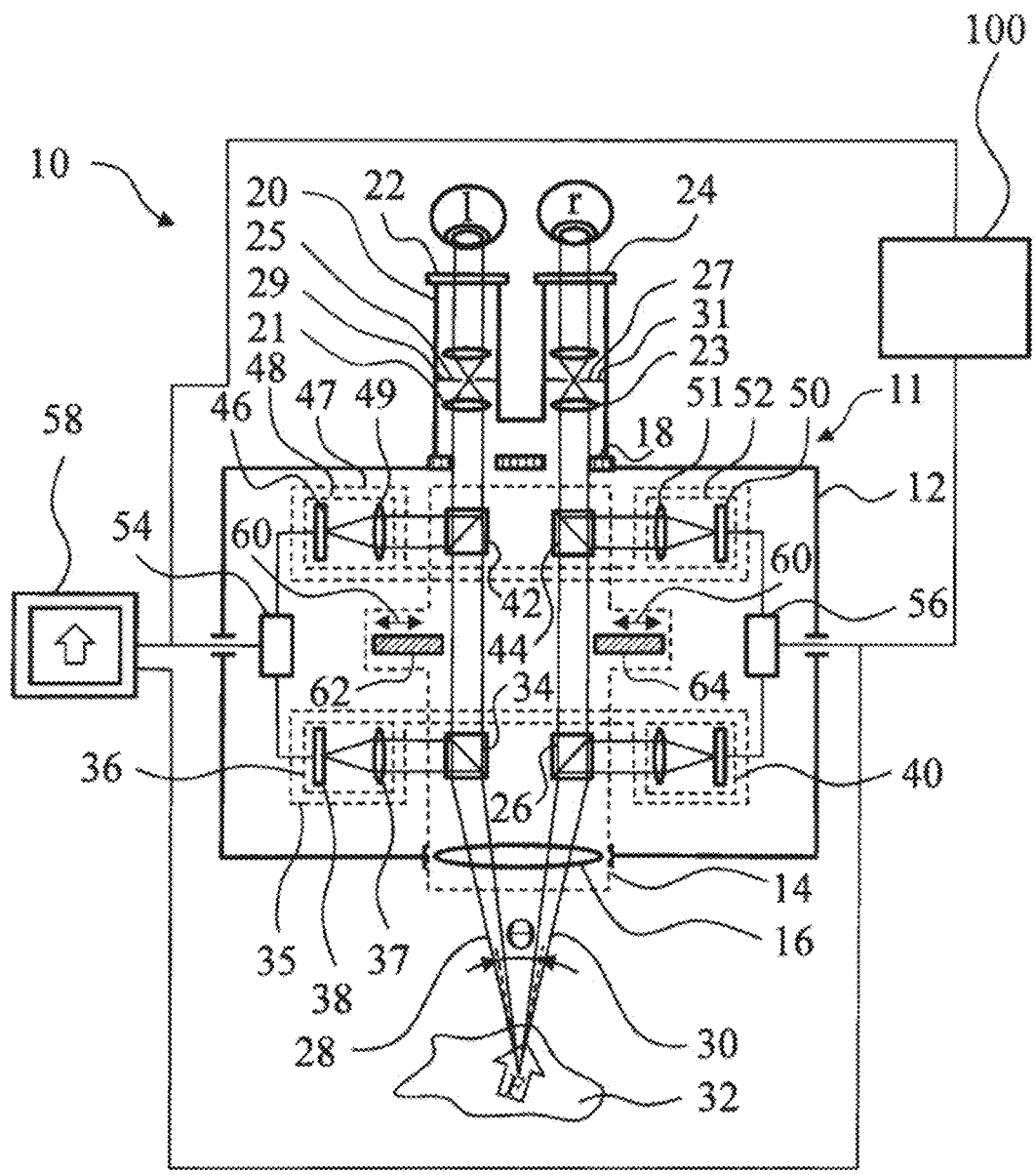
FIG. 1 shows a surgical system with a stereoscopic surgical microscope according to an embodiment of the invention.

The surgical system 10 shown in FIG. 1 includes a surgical microscope 11 with a main operating-microscope body 12, in which a switchable imaging optical unit 14 with a main microscope objective system 16 is accommodated. It has a binocular tube 20, which is connected to the main body 12 at an interface 18 and includes a first and a second eyepiece (22, 24) for a left and right eye (72, 74) of an observer. The main microscope objective system 16 in the surgical microscope 11 is passed through by a first observation beam path 28 and a second observation beam path 30 from an object region 32.

The imaging optical unit 14 includes an output coupling beam splitter 34, which is arranged in the first optical observation beam path 28, on the side of the main microscope objective system 16 that is facing away from the object region 32, and couples out part of the observation light from the first observation beam path 28 and sends it to an image acquisition device 35. The image acquisition device 35 includes a first image acquisition assembly 36 with an objective lens system 37 and an image sensor 38 and also a second image acquisition assembly 40 with an objective lens system 37 and an image sensor 38.

In addition, the imaging optical unit 14 has a further output coupling beam splitter 26, which is arranged in the second optical observation beam path 30, on the side of the main microscope objective system 16 that is facing away from the object region 32, and couples out part of the observation light from the second observation beam path 30 and sends it to the image acquisition device 35 with the objective lens system 37 and to the image sensor 38.

In the imaging optical unit 14 there is a first input coupling beam splitter 42 and a second input coupling beam splitter 44. By way of the input coupling beam splitters (42, 44,) display information that is displayed on a display 46 of a display assembly 48 of a display device 47 and on a display 50 of a display assembly 52 of the display device 47 can be overlaid on the image of the object region 32 in the first optical observation beam path 28 and in the second optical observation beam path 30.

Via the input coupling beam splitters (42, 44,) as described at the beginning, in particular an overlay image with image information from intraoperative modalities can be overlaid on the image of the object region 32 that is sent to the eyepiece 22 and the eyepiece 24 of the binocular tube 20.

For this, the display information (46, 50) of the display assemblies (48, 52) is in each case transferred by a display lens (49, 51) into a parallel beam path and projected via the tube lenses (21, 23) into the left and right intermediate image planes (25, 27) of the binocular tube 20. The intermediate image in the left and right intermediate image planes (25, 27) is delimited by an eyepiece field stop (29, 31) in the binocular tube 20. The imaging scale of the images of the displays (46, 50) in the left and right intermediate image planes (25, 27) is in this case determined by the ratio $f_D/f_T$ of the focal length $f_D$ of the display lenses (49, 51) and the focal length $f_T$ of the tube lenses (21, 23).

For activating the displays (46, 50), the surgical system 10 includes an image processing device 54 and an image processing device 56, which are connected to a data processing unit 100, which may be arranged inside or outside the main microscope body 12.

In order to display the images of the object region 32 that are acquired via the image acquisition devices (35, 40) from the first and second observation beam paths (28, 30), the surgical system 10 has an image reproducing device 58, which is preferably formed as a 3D monitor and is connected to the image processing devices (54, 56).

The imaging optical unit 14 of the surgical microscope 11 includes a shutter element 62 and a shutter element 64. The shutter elements (62, 64) can be displaced via a drive (not shown) in a way corresponding to the double-headed arrow 60. It is possible via the shutter elements (62, 64) to clear or block the first and/or second optical observation beam path (28, 30) on the side of the output coupling beam splitter (34, 26) that is facing away from the main microscope objective system 16.

In the operating state of the surgical system 10 that is shown in FIG. 1, the imaging optical unit 14 has been switched in such a way that the shutter elements (62, 64) clear the first and second optical observation beam paths (28, 30). Then, the optical observation beam paths 28 and 30 from the object region 32 that pass through the main microscope objective system 16 are respectively sent to the first and second eyepieces (22, 24) of the binocular tube 20 in the surgical microscope 11.

Figure 2:
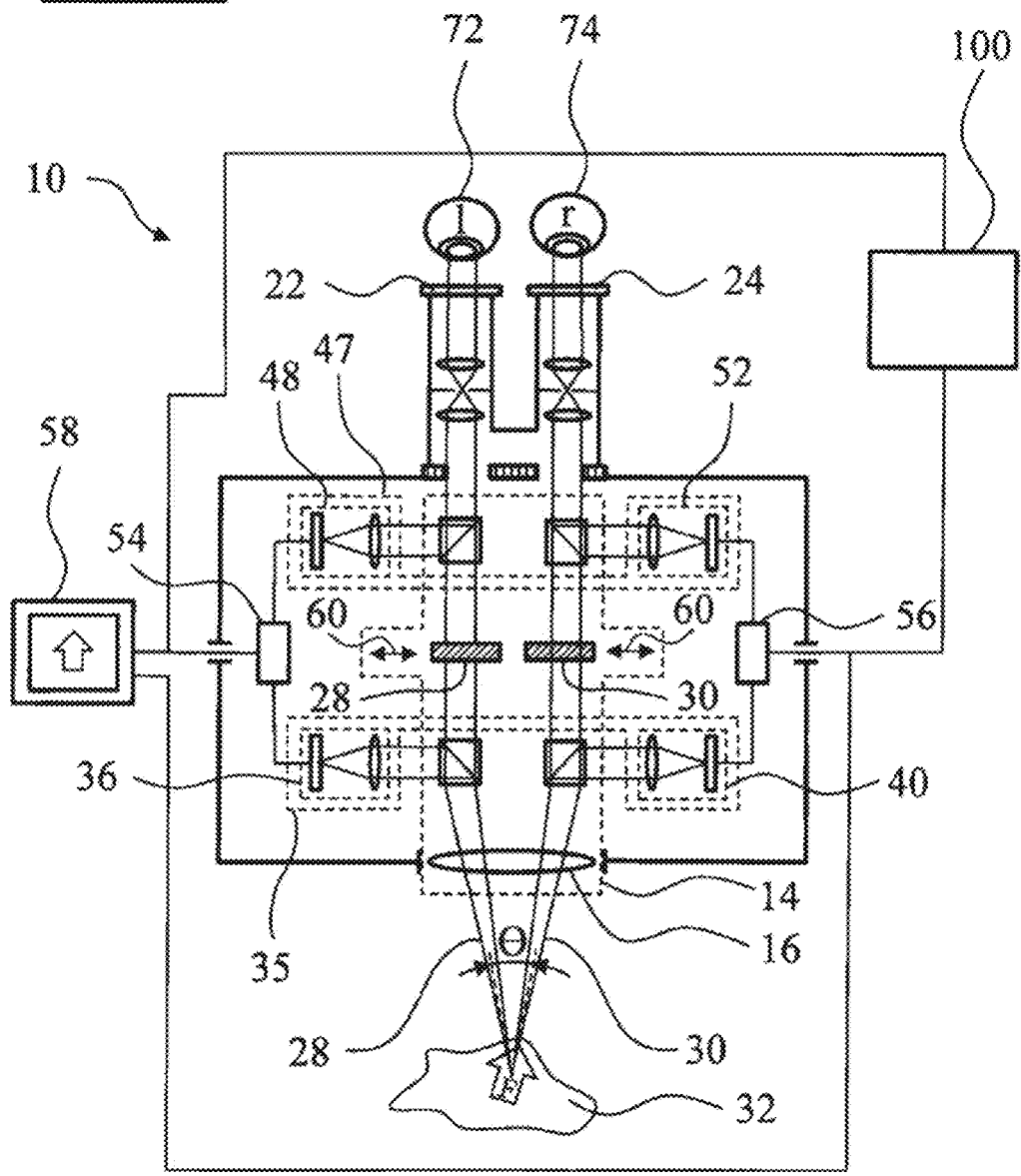
FIG. 2 shows the surgical system of FIG. 1 in another operating state.

FIG. 2 shows the surgical system 10 in a further operating state, in which the shutter elements (62, 64) block the first and second optical observation beam paths (28, 30). Here, the image of the object region 32 that is acquired via the image acquisition assemblies 36 and 40 of the image acquisition device 35 and is displayed by the display devices (48, 52) is respectively sent to the first and second eyepieces (22, 24) of the binocular tube 20 in the surgical microscope 11.

Therefore, the image acquisition assembly 36 of the image acquisition device 35 can be sent a left stereoscopic partial image of the object region 32 by the first optical observation beam path 28 and the image acquisition assembly 40 of the image acquisition device 35 can be sent a right stereoscopic partial image of the object region 32 by the second optical observation beam path 30. The optical axes of the two optical observation beam paths (28, 30) thereby form a stereo angle $\theta$. This makes it possible to stereoscopically display the object region 32 with the surgical microscope 11 even when the first and second observation beam paths (28, 30) are blocked via the shutter elements (62, 64). For this, the left stereoscopic partial image in the binocular tube 20 is then generated by the display assembly 48, and the right stereoscopic partial image by the display assembly 52, of the display device 47.

Figure 3:
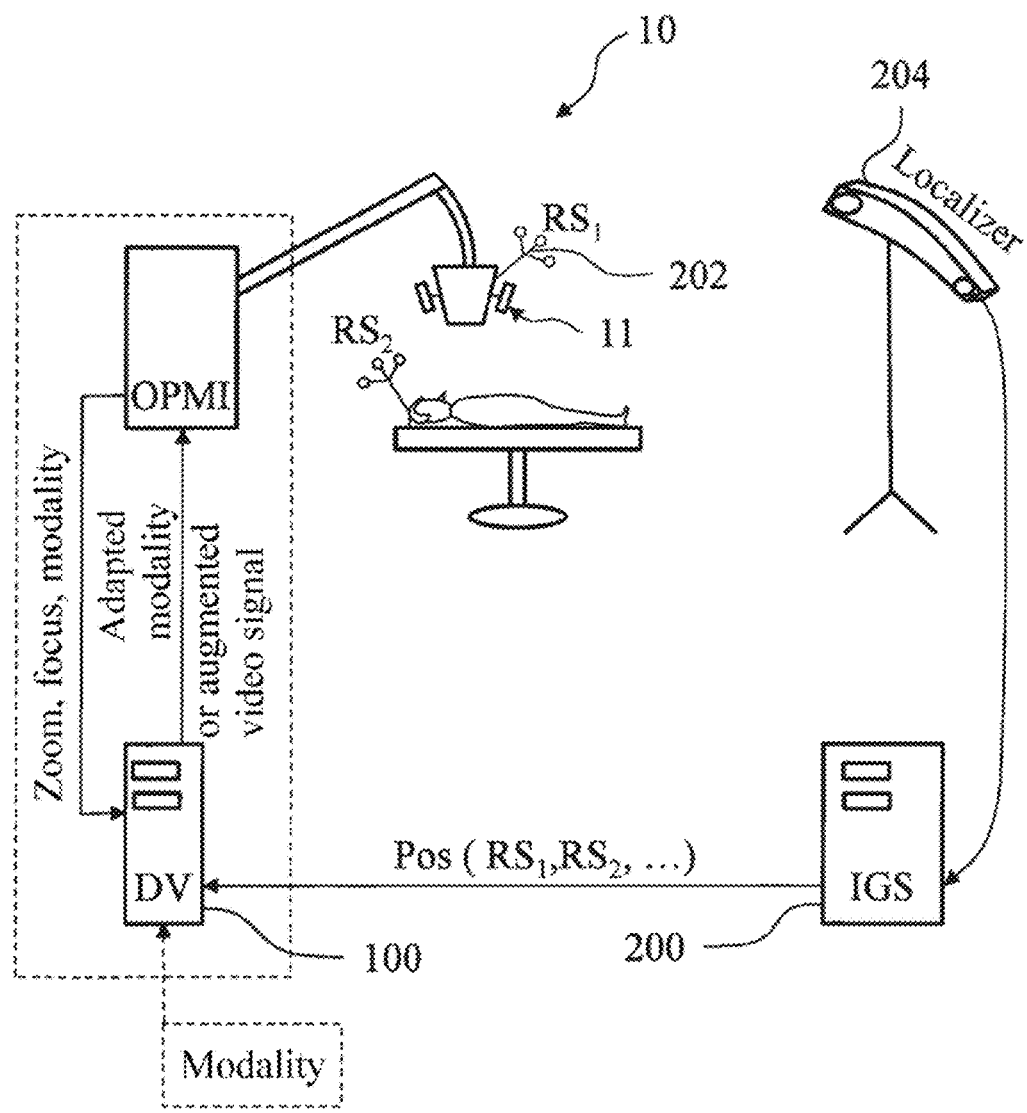
FIG. 3 is a schematic representation of a further embodiment of a surgical system according to the invention.

FIG. 3 shows an example of a surgical system 10 which, in addition to the surgical microscope 11 and the data processing unit 100 described above is also provided with a positioning system 200, which can acquire the position and spatial orientation of the surgical microscope 11 via one or more positioning markers 202 mounted on the surgical microscope 11 and via a position acquisition unit 204. As described below, the positioning system 200 can transfer the acquired position data to the data processing unit 100.

Figure 4:
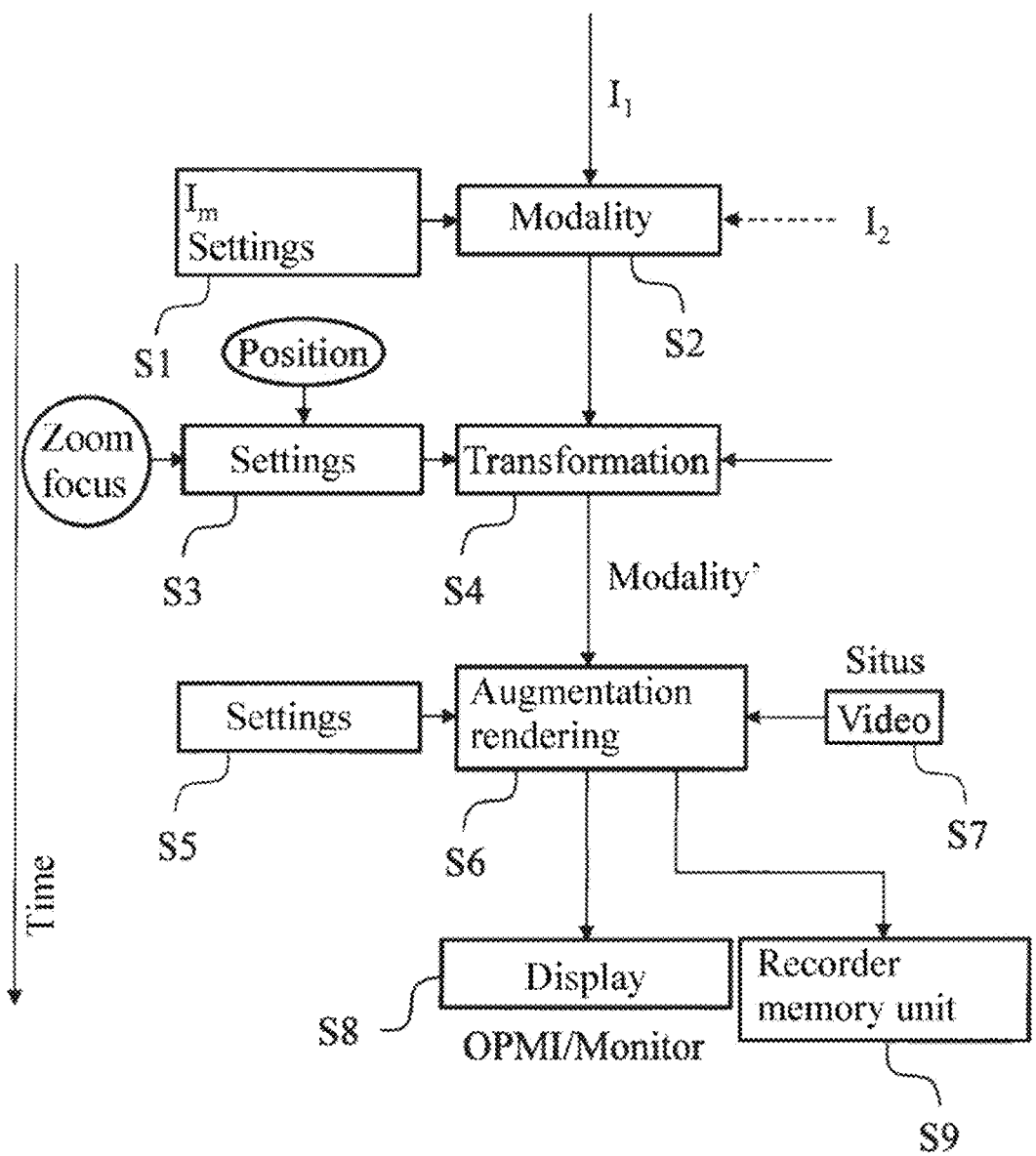
FIG. 4 shows the workflow of a method according to the invention.

FIG. 4 shows an example of a method according to an embodiment. Here, the settings required for the augmentation are stored in each case before an action (change of position, zoom, focus, modality, . . . ) is performed on the surgical microscope. Firstly, in step S1, the surgical microscope is operated in a first mode and an intraoperative modality is determined and stored (step S2). Subsequently, an action is triggered on the surgical microscope, such as for example the actuation of a button for switching over the modality, releasing the brakes, changing the zoom or focus setting, et cetera.

Before the action is initiated, in step S3 the data required for navigation are inquired from the internal sensors (focus value, zoom value, position values, . . . ) and provided with a time stamp. If the data are not instantaneously available in the internal communication bus of the OPMI, a corresponding request is sent with a unique time stamp/ID, so that incoming replies can be assigned to the time stamp. At the same time, if there is a positioning system, a request is also sent to it, to inquire the relative position between the surgical microscope and the patient.

This request is assigned the same time stamp, so that the value provided by the positioning system for the position can be assigned to the associated values of the imaging parameters even if the reply from the positioning system is delayed slightly. At the same time, there may also be a built-in timeout, in order to minimize the risk of a delay if the positioning system does not reply.

This value is then used in step S4, in order in response to the then following changes of the imaging parameter to adapt the augmentation correspondingly, for example to adapt the magnitude in the case of zoom changes, or in order to adapt the spatial orientation to a positional change of the surgical microscope. At the earliest after the time stamp has been created and the sending of the corresponding requests initiated, in step S5 the original action is performed. This ensures that the last valid value in each case of an imaging parameter before a change has been stored in the central data processing unit. Then, in step S6, the overlay image can be rendered with the modified modality determined in step S4. As described above in conjunction with FIG. 1, here the overlay image may be fed into the beam path between the main objective and the eyepiece of the surgical microscope via beam splitters. Alternatively, as described in conjunction with FIG. 2, the image generated by the main objective may be recorded as a video signal (step S7) and overlaid in an image processing device with the overlay image, which may likewise take the form of a video signal.

Finally, the overlaid image may for example be displayed on a monitor connected to the surgical microscope (step S8) or may be recorded and stored in a memory element (step S9).

The modalities and the main settings of the surgical microscope 11 can be made available to the central data processing unit 100. Then, the validity of the augmentation can be retained over a longer time period. The modality may be generated here on any other desired data processing unit, that is, for example also on the image processing devices (54, 56) in the surgical microscope 11. However, it is also possible to generate the modality on the central data processing unit 100.

In principle, it does not matter whether the augmentation is purely video-based, or is implemented as an overlay of an optical image and an electronically generated image. In the latter case, even the video signal of the situs is not required.

The central data processing unit 100 may be integrated in the surgical microscope 11, but may also be made available at any desired location outside the surgical microscope 11. However, it should advantageously be ensured that the video signal to be displayed or the adapted modality is available to the physician on a display device without any significant time delay. Providing these "without any significant time delay" depends here on the respective modality/application and may extend from several milliseconds to seconds.

Imaging parameters and settings of the surgical microscope are for example the zoom, focus or positions of the surgical microscope and the patient (it being possible for the position to include in each case the spatial orientation and alignment, for example described by a position vector and normal vector). If it is ensured that the patient is not moving, it is also possible to use only the position and change in alignment of the surgical microscope for the conversion.

The generated modality may also take the form of a 3D data set, the spatial orientation and alignment also being known from the position/alignment measurement of the surgical microscope and of the patient. This can be rendered for virtually any desired alignments. If the generated modality only takes the form of a 2D or 1D data set, new alignments of the surgical microscope 11 can only be taken into account by a projection of the modality onto the new alignment.

If a modality is not continuously acquired, according to some embodiments the validity of its augmentation may depend on certain factors that are different for each modality. The more these factors change, the greater the disparity between the overlay image and reality becomes. According to an embodiment, it may be envisaged to abandon the augmentation on account of the changing of the respective factors or to mark it as no longer necessarily relevant.

Figure 5:
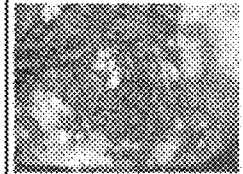
FIG. 5 shows an example of an application of the system and the method according to the invention during an operation.
Figure 5:
Figure 5:
Figure 5:
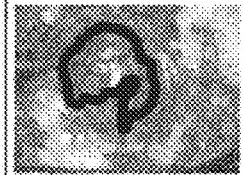
Figure 5:
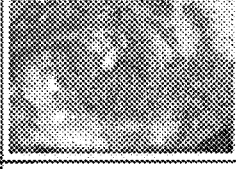
Figure 5:
Figure 5:
Figure 5:
Figure 5:

FIG. 5 shows an example of an application of the system and method according to the invention in the representation of a tumor margin. A marginal contour of a tumor is calculated from the color information of a fluorescent image. As is evident from FIG. 5 and the following description, this contour can be easily adapted when there are changes of the zoom. Changes of the optical axis of the surgical microscope can no longer be corrected as easily. If part of the tumor is then removed, the contour is no longer adaptable.

According to an embodiment, one or more imaging parameters or factors may therefore be determined for a modality. Limit values for the maximum change since the last determination may then be determined, individually and in combination, for these imaging parameters or factors. If the changes of the value of the imaging parameter reach one of these limit values, the augmentation becomes invalid. This can be brought to the attention of the user by abandonment of the augmentation, by lessening of the augmentation and/or by displaying a reliability parameter as a number or symbol (bar, color change).

The imaging parameters or factors include for example the time, zoom factor, movement of the optical axis, focus (image plane), use of tools (in general or of certain tools detected from the camera image), changing of the surgical scene captured by the camera (for example excessive deformation of the tissue).

The example represented in FIG. 5 shows:
1. In Blue 400 mode, the situs is recorded. The present position of the patient and the surgical microscope is requested for example from an external navigation device (or by some other solution for determining the relative position of the surgical microscope and the patient). The zoom, focus and illumination settings are likewise stored.
2. The tumor margin is continuously calculated from the color information of the fluorescent image. The tumor margin is valid for the respectively current alignment and focus/zoom setting of the surgical microscope. The tumor margin takes the form here for example of a 2D data set. The orientation of the patient is determined from the positions of the surgical microscope and the patient and the focal plane of the surgical microscope (differences in height are not taken into account in this example).
3. The surgical microscope is switched back to the white light mode. The last contour in each case and the associated values are stored as belonging together (for example by an ID or a time stamp) in the central data processing unit.
4. Then a value of an imaging parameter is changed.
   a. The value for the zoom setting is changed: in this case there is a simple conversion rule. The tumor margin must be scaled in a way corresponding to the zoom factor.
   b. The alignment of the surgical microscope is changed: in this case the modality must be converted to the new orientation and alignment of the surgical microscope.

The present surgical system makes it possible to feed intraoperative modalities, such as for example diagnostic data obtained intraoperatively via sensors, into a surgical microscope and overlap them with the image generated by the surgical microscope even when at least one imaging parameter, such as for example a zoom setting, focus value or position of the surgical microscope, changes. Storing the parameter values, while also being able to assign a time stamp to the parameter values, means that it can continue to be ensured that a conversion rule for the adaptation of an overlay image that can be documented and replicated, even retroactively, can be determined at any point in time.

It is understood that the foregoing description is that of the preferred embodiments of the invention and that various changes and modifications may be made thereto without departing from the spirit and scope of the invention as defined in the appended claims.

What is claimed is:
1. A method for superimposing an overlay image with an image generated by a surgical microscope, the method comprising the steps of:
   operating the surgical microscope in a first mode;
   recording data obtained via sensors during the operation of the surgical microscope in the first mode;
   triggering an action on the surgical microscope;
   generating an overlay image from the recorded data;
   inquiring and storing a first value of at least one imaging parameter of the surgical microscope in a data processing unit, wherein the at least one imaging parameter includes at least one setting parameter for at least one of zoom, focus, position and a spatial alignment of at least one of the surgical microscope and a patient, and, wherein the stored first value of the at least one imaging parameter of the surgical microscope corresponds to a last valid value of the at least one setting parameter;
   providing said at least one imaging parameter with a time stamp;
   performing the action and changing the at least one imaging parameter;
   storing a second value of the at least one imaging parameter;
   modifying the overlay image in a manner corresponding to the stored first and second values of the at least one imaging parameter so as to generate a modified overlay image; and,
   overlaying the modified overlay image with the image generated by the surgical microscope.

2. The method of claim 1 further comprising the step of sending a request to an internal communication bus of the surgical microscope to inquire the first value of the at least one imaging parameter of the surgical microscope and assigning an incoming reply to the time stamp.

3. The method of claim 2 further comprising the steps of:
   sending a request to a positioning system to inquire a relative position between the surgical microscope and the patient; and, assigning an incoming reply to the time stamp;
wherein the request to the internal communication bus of the surgical microscope and the request to the positioning system are sent at the same time.

4. The method of claim 1 further comprising the steps of:
determining limit values for a maximum change of said at least one imaging parameter since the last determination; and,
abandoning or lessening of the overlay of the modified overlay image with the image generated by the surgical microscope, if a change of the value of the imaging parameter reaches the limit value.

5. The method of claim 1 further comprising the steps of:
determining limit values for a maximum change of said at least one imaging parameter since the last determination; and,
abandoning or lessening of the overlay of the modified overlay image with the image generated by the surgical microscope and displaying a reliability parameter as a number or symbol, if a change of the value of the imaging parameter reaches the limit value.

6. The method of claim 1 further comprising the steps of:
determining limit values for a maximum change of said at least one imaging parameter since the last determination; and,
displaying a reliability parameter as a number or symbol, if a change of the value of the imaging parameter reaches the limit value.

\* \* \* \* \*